United States Patent [19]

Eissenstat et al.

[11] Patent Number: 5,356,903

[45] Date of Patent: Oct. 18, 1994

[54] 1-CYCLOPROPYL-4-PYRIDYL-QUINO-LINES

[75] Inventors: Michael A. Eissenstat, West Sand Lake, N.Y.; Gee-Hong Kuo, Blue Bell, Pa.

[73] Assignee: Sterling Winthrop Inc., New York, N.Y.

[21] Appl. No.: 52,027

[22] Filed: Apr. 22, 1993

[51] Int. Cl.$^5$ ............................................. A61K 31/47
[52] U.S. Cl. ............................ 514/311; 514/313; 514/314; 546/159; 546/160; 546/161; 546/162; 546/163
[58] Field of Search ............ 514/311, 313, 314; 546/162, 159, 160, 161, 163

[56] References Cited

U.S. PATENT DOCUMENTS 4,623,650 11/1986 Gilligan et al. .
4,705,788 11/1987 Schriewer et al. .
4,908,366 3/1990 Schriewer et al. .
4,959,363 9/1990 Wentland .
5,075,319 12/1991 Lesher et al. .

*Primary Examiner*—José G. Dees
*Assistant Examiner*—Samuel Barts
*Attorney, Agent, or Firm*—Richard A. Hake; Paul E. Dupont

[57] ABSTRACT

Compounds of formula

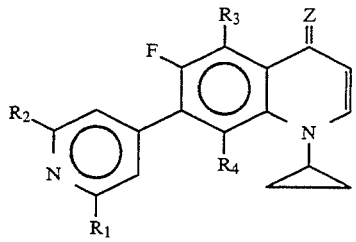

wherein;

$R_1$ is hydrogen, lower-alkyl, or trifluoromethyl;

$R_2$ is lower-alkyl, trifluoromethyl or $CH_2X$ where X is hydroxy, chloro, lower-alkylamino or dilower-alkylamino;

$R_3$ and $R_4$ are each individually hydrogen or fluoro;

Z is $NR_5$ or $CR_6R_7$;

$R_5$ is hydrogen, aryl, arylthio, arylsulfonyl, lower-alkyl, cycloalkyl, heterocycloalkyl, amino-lower-alkyl, lower-alkylamino-lower-alkyl, dilower-alkylamino-lower-alkyl, lower-alkoxy, hydroxy or $NR_8R_9$;

$R_6$ is hydrogen, cyano, lower-alkoxycarbonyl, lower-alkanoyl, nitro or lower-alkylsulfonyl;

$R_7$ is hydrogen, cyano, lower-alkoxycarbonyl, lower-alkanoyl, nitro, aryl, or lower-alkylsulfonyl;

$R_8$ is hydrogen, lower-alkyl, aryl, heterocycloalkyl, carbamyl, alkanoyl, aroyl, hydroxy-lower-alkyl; and $R_9$ is hydrogen, lower-alkyl or lower-alkanoyl or pharmaceutically acceptable acid addition salts thereof are useful as anticancer agents.

10 Claims, No Drawings

1-CYCLOPROPYL-4-PYRIDYL-QUINOLINES

BACKGROUND OF THE INVENTION a) Field of the Invention

This invention relates to novel 1-cyclopropyl-4-substituted-5-$R_3$-6-fluoro-8-$R_4$-7-(2-$R_1$-6-$R_2$-4-pyridyl)-1,4-dihydro-quinolines and their pharmaceutical compositions, and a method of treating malignancy with these compounds.

b) Information Disclosure Statement

Gilligan et al., U.S. Pat. No. 4,623,650 issued Nov. 18, 1986, discloses 1-substituted 6,8-difluoro-7-aryl-1,4-dihydroquinol-4-one 3-carboxylic acids stated to have antibacterial activity.

Schriewer et al., U.S. Pat. No. 4,705,788 issued Nov. 10, 1987, discloses antibacterially active 7-amino-1-(substituted cyclopropyl)-1,4-dihydro-4-oxo-3-quinolinecarboxylic acids of the formula

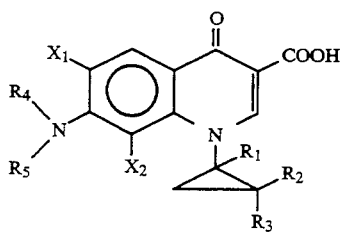

in which $X_1$ and $X_2$ can be identical or different and represent hydrogen or halogen;

$R_1$, $R_2$ and $R_3$ represent hydrogen, methyl, chlorine or fluorine, the radicals $R_1$–$R_3$ never all being identical; and $R_4$ and $R_5$, together with the nitrogen atom to which they are bonded, form a 5-membered or 6-membered heterocyclic ring which may be substituted.

Schriewer et al., U.S. Pat. No. 4,908,366, issued Mar. 13, 1990, discloses compounds of the formula

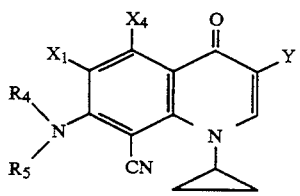

in which

Y represents a carboxyl group, a nitrile group, an ester group —$COOR_1$ or an acid amide group —$CONR_2R_3$;

$X_1$ represents hydrogen, nitro, alkyl or halogen;

$X_4$ can be hydrogen or halogen, or alkyl;

$R_4$ and $R_5$, together with the nitrogen atom to which they are bonded form a 5- or 6-membered heterocyclic ring which can additionally contain the atoms or groups —O—, —S—, —SO—, —SO$_2$—,

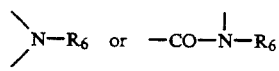

as ring members of the group

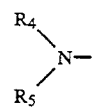

can also represent a ring system of the structure

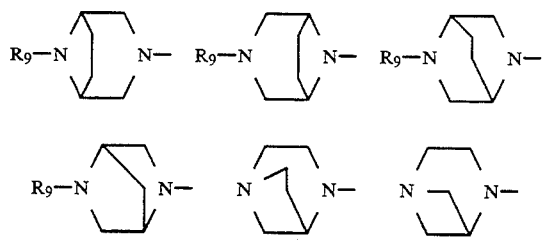

which can optionally be substituted on the ring carbons by methyl and pharmaceutically usable hydrates, salts or esters thereof.

These compounds are stated to have a high antibacterial activity and therefore to be suitable as active compounds for human and veterinary medicine.

Wentland, U.S. Pat. No. 4,959,363, issued Sep. 25, 1990, discloses compounds of the formula

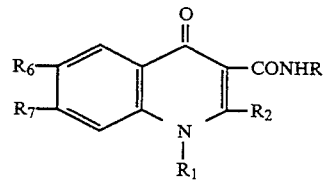

where

R is hydrogen, hydroxy, amino or lower-alkyl;

$R_1$ is lower-alkyl, lower-alkenyl, cycloalkyl, pyridinyl, phenyl or substituted phenyl $R_2$ is hydrogen, amino or hydroxy;

$R_6$ is hydrogen or fluoro; and $R_7$ is phenyl, pyridinyl or selected other heterocycles; The compounds are stated to have antiviral activity against herpes virus.

Lesher et al., U.S. Pat. No. 5,075,319, dated Dec. 24, 1991, discloses fluorinated 1-cyclopropyl-7-(substituted-pyridinyl)-1,4-dihydro-4-oxo-3-quinolinecarboxylic acids of the formula

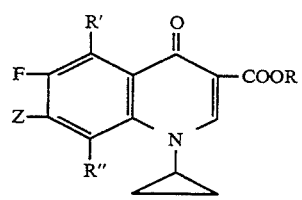

wherein

R is hydrogen;

R' and R" are hydrogen or fluoro, or other groups; and

Z is 3- or 4-pyridinyl substituted by alkyl groups or substituted alkyl groups. The compounds are stated to be superior antibacterial agents.

SUMMARY OF THE INVENTION

The invention resides in one aspect in novel 1-cyclopropyl-4-substituted-5-$R_3$-6-fluoro-8-$R_4$-7-(2-$R_1$-6-$R_2$-4-pyridyl)-1,4-dihydroquinolines useful as antineoplastic agents.

In another aspect, the invention relates to intermediates useful in the preparation of the novel 1-cyclopropyl-4-substituted-5-$R_3$-6-fluoro-8-$R_4$-7-(2-$R_1$-6-$R_2$-4-pyridyl)-1,4-dihydroquinolines.

In another aspect, the invention relates to pharmaceutical compositions containing as an active ingredient 1-cyclopropyl-4-substituted-5-$R_3$-6-fluoro-8-$R_4$-7-(2-$R_1$-6-$R_2$-4-pyridyl)-1,4-dihydroquinolines and their pharmaceutically acceptable salts.

In yet another aspect, the invention relates to a method of inhibiting the growth of or killing malignant cells in a mammal afflicted with malignant cells, which comprises administering to said mammal an effective amount of a compound of the invention or a pharmaceutically acceptable salt thereof or composition of the invention in an effective amount to inhibit the growth or induce the regression of these cells.

DETAILED DESCRIPTION INCLUSIVE OF PREFERRED EMBODIMENTS

More specifically the invention relates to compounds of formula I;

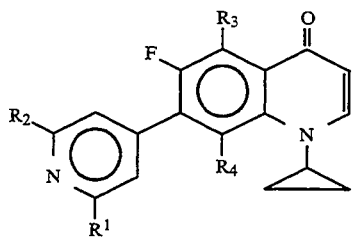

wherein $R_1$ is hydrogen, lower-alkyl, or trifluoromethyl;

$R_2$ is lower-alkyl, trifluoromethyl or $CH_2X$ where X is hydroxy, chloro, lower-alkylamino or dilower-alkylamino;

$R_3$ and $R_4$ are each individually hydrogen or fluoro;

Z is $NR_5$ or $CR_6R_7$;

$R_5$ is hydrogen, aryl, arylthio, arylsulfonyl, lower-alkyl, cycloalkyl, heterocycloalkyl, amino-lower-alkyl, lower-alkylamino-lower-alkyl, dilower-alkylamino-lower-alkyl, lower-alkoxy, hydroxy or $NR_8R_9$;

$R_6$ is hydrogen, cyano, lower-alkoxycarbonyl, lower-alkanoyl, nitro or lower-alkylsulfonyl;

$R_7$ is hydrogen, cyano, lower-alkoxycarbonyl, lower-alkanoyl, nitro, aryl, or lower-alkylsulfonyl;

$R_8$ is hydrogen, lower-alkyl, aryl, heterocycloalkyl, carbamyl, alkanoyl, aroyl, hydroxy-lower-alkyl; and $R_9$ is hydrogen, lower-alkyl or lower-alkanoyl or pharmaceutically acceptable acid addition salts thereof.

Aryl refers to monocyclic 5 or 6 membered or bicyclic 9 or 10 membered, or tricyclic 12–15 membered aromatic or heteroaromatic radicals, bicyclic and tricyclic aryl having about 5 to about 6 atoms in each ring. A heteroaromatic radical is defined as having carbon and one or more of oxygen, nitrogen or sulfur within the ring for example, pyrimidyl, pyridyl, acridinyl, quinolyl, indolyl, furanyl, tetrazolyl, oxadiazolyl, thiazolyl, thiadiazolyl, and the like. These heteroaromatic radicals (heteroaryl) may be substituted with lower-alkyl, lower-alkanoyl, hydroxy, lower-alkanoyloxy, lower-alkoxycarbonyl, amino, lower-alkoxy, lower-alkylamino, dilower-alkylamino or halo.

As used herein the term lower-alkyl refers to a saturated hydrocarbon radical having from 1 to about 4 carbons, for example methyl, ethyl, propyl, isopropyl, butyl and the like.

Lower-alkoxy refers to alkyloxy having from 1 to about 4 carbon atoms, for example, methoxy, ethoxy, propoxy, butoxy, sec-butoxy.

Lower-alkanoyl refers to lower-alkylcarbonyl in which lower-alkyl is as defined above, for example, acetyl, propionyl, butyryl, valeryl and the like.

As used herein alkanoyloxy refers to lower-alkylcarbonyloxy radicals wherein lower-alkyl is as defined above. Examples include acetyloxy, propionyloxy, valeryloxy, butyryloxy and the like.

As used herein lower-alkoxycarbonyl refers to a straight or branched lower-alkoxycarbonyl radical having from two to about five carbons, for example, methoxycarbonyl, ethoxycarbonyl, isopropoxycarbonyl and the like.

As used herein cycloalkyl refers to a cyclic saturated hydrocarbon radical having from 3 to about 7 carbons, for example cyclopropyl, cyclobutyl, cyclopentyl, cyclohexyl, cycloheptyl and the like.

As used herein heterocycloalkyl refers to a 5 or 6 membered cyclic saturated radical having carbon and having one or more of nitrogen, oxygen or sulfur in the cyclic chain, for example morpholinyl, piperidinyl and the like.

As referred to herein the term halo refers to the four common halogens, fluoro, chloro, bromo or iodo.

Preferred compounds of formula I are those of the formula;

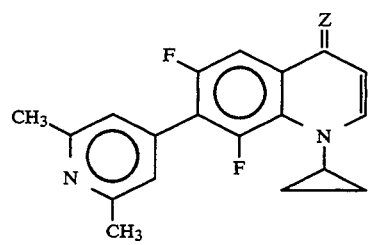

Compounds of formula I are prepared via Intermediate A, which in turn is obtained from the known acid, whose preparation is disclosed in U.S. Pat. No. 5,075,319, by one of three methods:

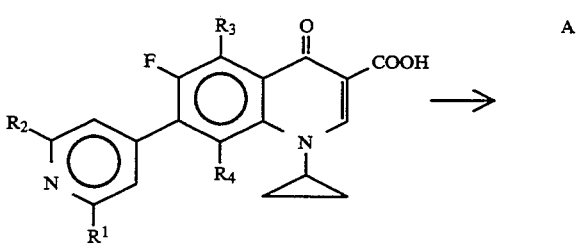

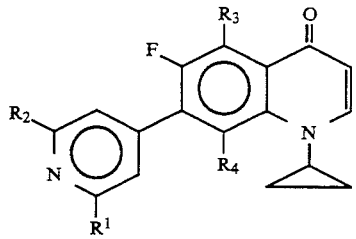

The known quinolinone carboxylic acid is decarboxylated by known methods, for example copper in refluxing quinoline, to afford Intermediate A.

Compounds of formula I where Z is $NR_5$ wherein $R_5$ is $NR_8R_9$ may be obtained by reacting Intermediate B with a known hydrazine, preferably in an inert solvent at a temperature between 0° C. and the boiling point of the reaction mixture, for a sufficient time to observe the appearance of product or the disappearance of starting materials as determined by methods known in the art, for example TLC and the like. In a preferred method, compounds of formula I where Z is $NR_5$, and $R_5$ is cycloalkyl, lower alkyl, heterocycloalkyl, amino-lower-alkyl, lower-alkylamino-lower-alkyl, or dilower-alkylamino-lower-alkyl, or $NR_8R_9$ are prepared according to the general scheme;

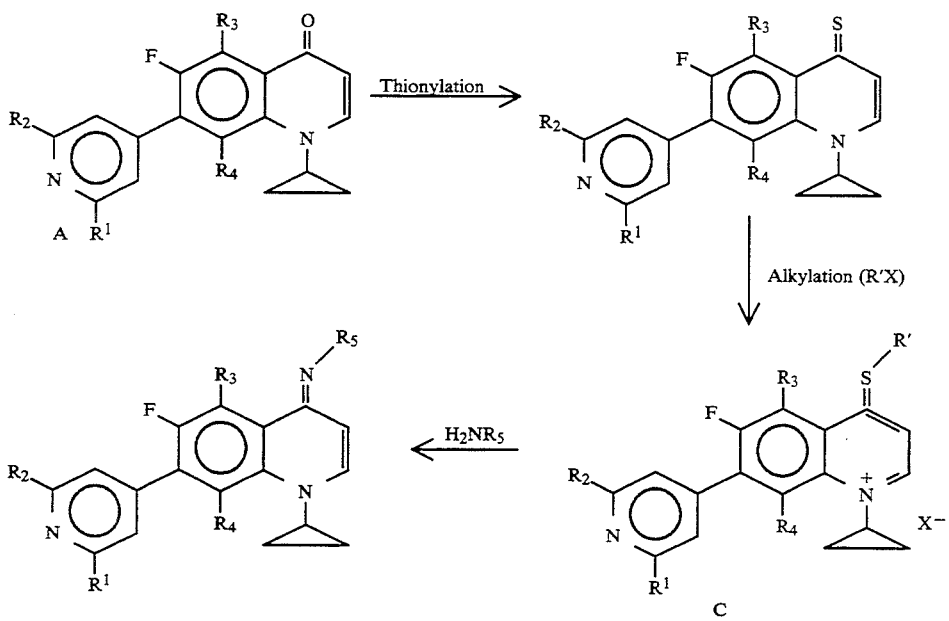

Wherein R' is lower-alkyl and X is halo, tosylate or other good leaving group.

The 4-alkylthio quinoline C is reacted with a known primary amine, ($R_5NH_2$) or hydrazine ($R_9R_8NNH_2$) in an inert solvent in the presence of a base, in a preferred method, an organic base, for example, pyridine, triethylamine, or the like, or the primary amine or the hydrazine itself, for example pyridyl hydrazine and the like, may serve as the solvent. The mixture is then reacted at a temperature between 0° C. and the reflux temperature of the solvent until desired products appear or starting materials disappear as determined by conventional detection methods, for example thin layer chromatography (TLC) and the like.

The hydrazines, $R_9R_8NNH_2$, as well as the primary amines ($R_5NH_2$) used as starting materials are either commercially available, known or may be prepared by procedures known in the art. The resulting $R_5$ may be altered by conventional means well known in the art, such as acid hydrolysis, amidation, esterification and the like.

Intermediate C is prepared by the reaction of an alkylating agent (R'X) with quinolinethione B, at a temperature between ambient temperature and the boiling point of the mixture until products appear or starting materials disappear as determined by conventional methods, for example TLC and the like. In a prefered method, the reaction is carried out in an inert solvent.

Intermediate B is prepared by reaction of known Intermediate A and a thionylating reagent, for example, [2,4-bis-(4-methoxyphenyl)1,3-dithia-2,4-diphosphetane-2,4-disulfide] (Lawesson's Reagent), $P_4S_{10}$ and the like.

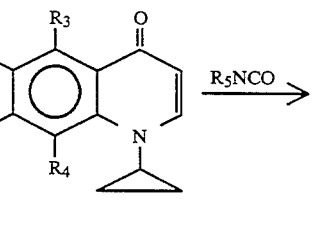

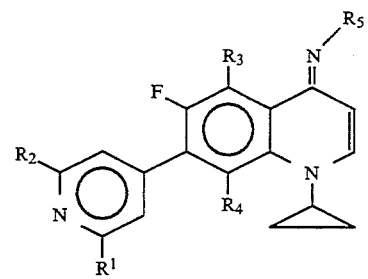

Compounds of formula I wherein Z is $NR_5$ and $R_5$ is cycloalkyl, lower-alkyl, aryl or arylsulfonyl are prepared by reaction of Intermediate A with known isocyanates ($R_5NCO$), preferably in an inert solvent at a temperature between 0° C. and the boiling point of the reaction mixture, for a sufficient time to observe the appearance of product or the disappearance of starting materials as determined by methods known in the art, for example TLC and the like. The resulting $R_5$ may be altered by means well known in the art, such as acid hydrolysis and the like.

Compounds of formula I wherein Z is $CR_6R_7$ are prepared by reaction of Intermediate A with a molecule having a nucleophilic carbon, for example malonitrile, nitromethane, $C_6H_5CH_2NO_2$, $CH_2(SO_2CH_2CH_3)_2$, $NCCH_2COOCH_2CH_3$ and the like, in the presence of a dehydrating agent such as acetic anhydride and the like, at a temperature from 0° C. to the boiling point of the reaction mixture, until products appear or reactants disappear as determined by conventional means, such as TLC. The resulting $R_6$ and $R_7$ substituents may be manipulated by conventional means.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; cleavage of methyl or benzyl ethers to produce the corresponding alcohols or phenols; decarboxylation of $\alpha,\beta$ unsaturated acids; and hydrolysis of esters or amides to produce the corresponding acids, alcohols or amines as desired, can be carried out. It will also be appreciated that certain of these transformations may require well recognized protection of certain functional groups, the reader will appreciate that this falls well within the scope of the skills of the practitioner skilled in the art.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anion. In practicing the present invention, it is convenient to form the hydrochloride, fumarate, toluenesulfonate, hydrogen sulfate, methanesulfonate or maleate salts and the like. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, or mass spectroscopy. The course of the reactions and the identity and homogeneity of the products were assessed by thin layer chromatography (TLC) and high-pressure liquid chromatography (HPLC) and melting point.

The following examples illustrate the invention, but however do not limit it thereto.

Preparation of Intermediates

Preparation 1

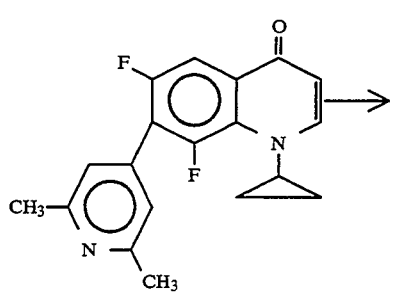

Intermediate A'

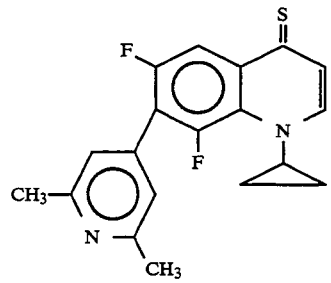

Intermediate B'

4 g (12.3 mmol) Intermediate A'(formula A: $R_1=R_2=CH_3$; $R_3=$Hydrogen; $R_4=$Fluoro), 5.45 g (13.5 mmol) Lawesson's Reagent were taken up in 200 ml dry toluene and refluxed 5 hours. The solvent was stripped off and the residue taken up in methylene chloride which was then adsorbed onto a silica gel column and eluted with 1/1 ethyl acetate/hexane. Recrystallization from methylene chloride/hexane yielded 3.45 g (82%) of the desired thione product, Intermediate B' (formula B: $R_1=R_2=CH_3$; $P_3=$Hydrogen; $R_4=$Fluoro) as an orange solid, m.p. 240°–243° C.

Preparation 2

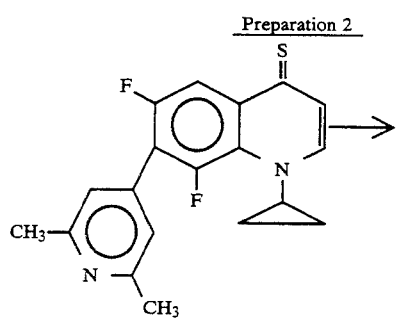

Intermediate B'

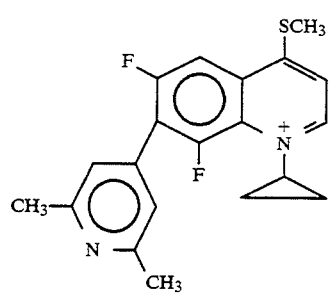

Intermediate C'

1.56 g (4.38 mmol) of Intermediate B' (formula B: $R_1=R_2=CH_3$; $R_3=$Hydrogen; $R_4=$Fluoro) and 3 ml methyl iodide were taken up in 60 ml THF and stirred at room temperature for 6 hours. The product was collected by filtration and washed with ethyl acetate thrice and dried at 60° C. for 24 hours to give 1.79 g (84%) of the product as an orange red solid, Intermediate C' (formula C: $R_1=R_2=CH_3$; $R_3=$Hydrogen; $R_4=$Fluoro; $R'=CH_3$; $X^-=I^-$). m.p. 210° C. (decomposed)

EXAMPLE 1 (Method A)

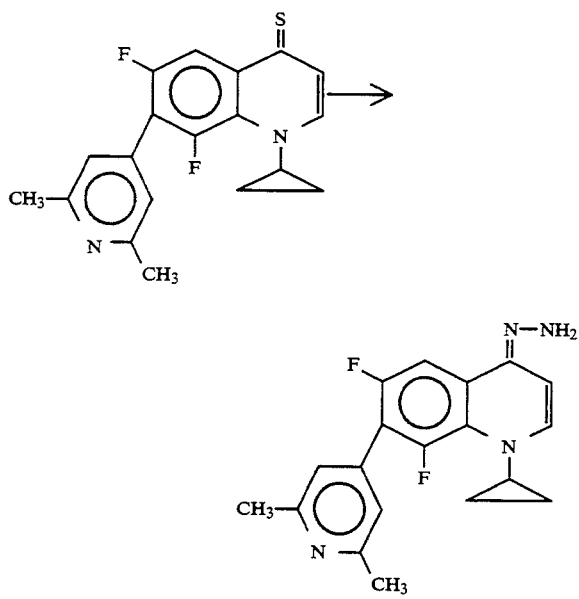

1 g (2.92 mmol) of Intermediate B' (formula B: $R_1=R_2=CH_3$; $R_3=$Hydrogen; $R_4=$Fluoro) and 1.46 g (29.2 mmol) of hydrazine hydrate were taken up in 20 ml of THF and refluxed for 2 hours. The solvent was stripped off and the residue taken up in methylene chloride. The product was purified by silica gel chromatography, eluting with methylene chloride/methanol (22/1) yielding 0.67 g (68%) of a compound of formula I ($R_1=R_2=CH_3$; $R_3=$Hydrogen; $R_4=$Fluoro; $Z=NR_5$; $R_5=NH_2$); m.p 108° C. (decomposed)

EXAMPLE 2 (Method B)

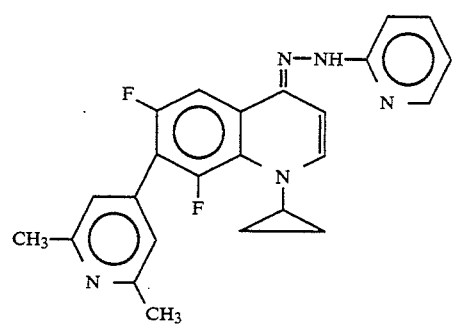

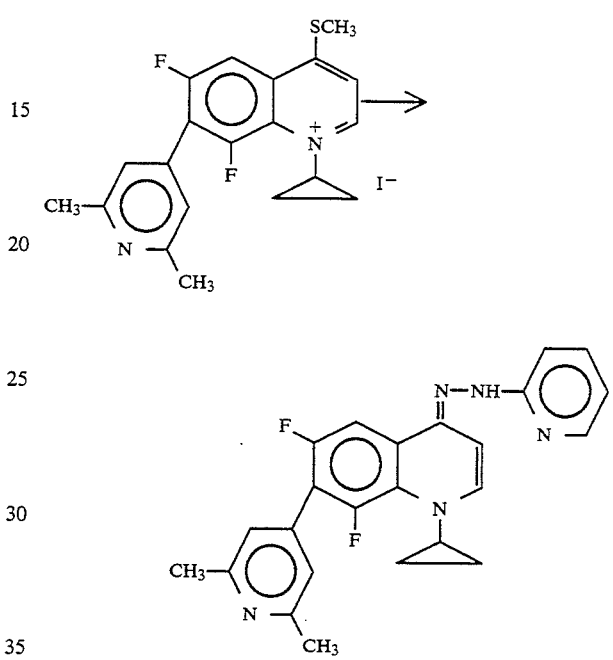

300 mg of Intermediate C' (formula C: $R_1=R_2=CH_3$; $R_3=$Hydrogen; $R_4=$Fluoro; $R'=CH_3$; $X^-=I^-$) was taken up in 10 ml ethanol and heated to 50° C. To this solution 135 mg (1.24 mmol) 2-hydrazinopyridine was added and the mixture was stirred at 50° C. for an additional 21 hours. The solvent was stripped off and the residue taken up in methylene chloride/methanol and adsorbed onto a silica gel column. A gradient of ethyl acetate/hexane (1/1) to pure ethyl acetate eluted 185 mg orange product. This product was recrystallized from ethyl acetate/hexane to give 162 mg (63%) of a red solid. mp 130°-133° C. (formula I: $R_1=R_2=CH_3$; $R_3=$Hydrogen; $R_4=$Fluoro; $Z=NR_5$; $R_5=$2-pyridylamino)

EXAMPLE 3 (Method C)

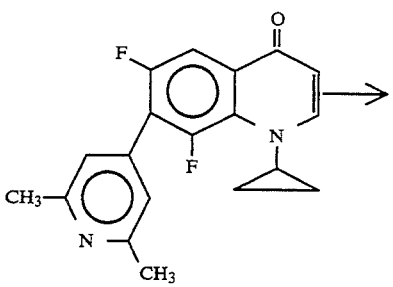

-continued

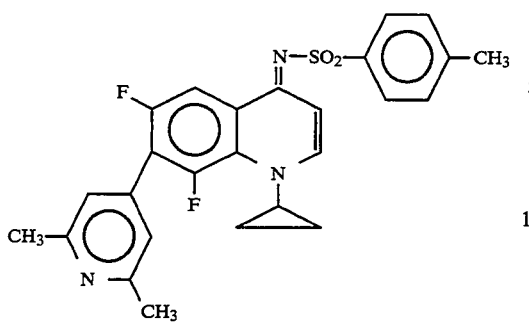

326 mg (1.0 mmol) of Intermediate A' (formula A; $R_1=R_2=CH_3$; $R_3=$Hydrogen; $R_4=$Fluoro), 0.4 ml of tosyl isocyanate and 10 ml toluene were refluxed for 4 hours. The reaction mixture was concentrated in vacuo and taken up in ethyl acetate. The ethyl acetate phase was washed three times with 2N NaOH, dried (MgSO$_4$), concentrated, applied to a silica gel column and eluted with ethyl acetate. The product was recrystallized from methylene chloride/ethyl acetate to give 414 mg (86%) of a pale yellow solid, a compound of formula I, ($R_1=R_2=CH_3$; $R_3=$Hydrogen; $R_4=$Fluoro; $Z=NR_5$; $R_5=SO_2C_6H_4CH_3$) melting point 204°–205° C.

EXAMPLE 4

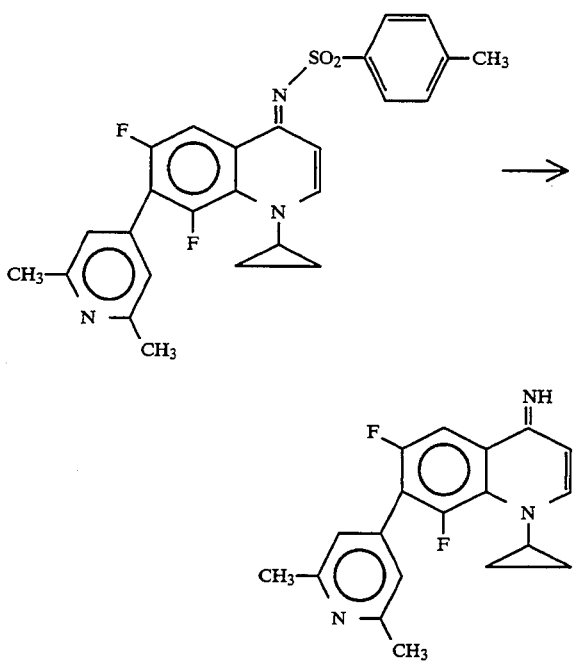

135 mg phenol was dissolved in 4 ml 48% HBr and heated to 50° C.; 240 mg of Example 3 was added and the reaction mixture heated to 80°–90° C. for 8 hours. The reaction mixture was cooled and basified with NaOH and extracted thrice with ethyl acetate. The organic portions were pooled and washed thrice with 2N NaOH, dried and concentrated in vacuo to an oil. The oil was crystallized from ether to give 55 mg (34%) of the desired product as a solid, collected by filtration. The filtrate was treated with ethereal HCl. The HCl addition salt was recrystallized from ethyl acetate/ethanol to give 78 mg (40%) of the HCl addition salt of a compound of formula I, ($R_1=R_2=CH_3$; $R_3=$Hydrogen; $R_4=$Fluoro; $Z=NR_5$; $R_5=H$) The combined yield of base and hydrochloride was 74%.

EXAMPLE 5

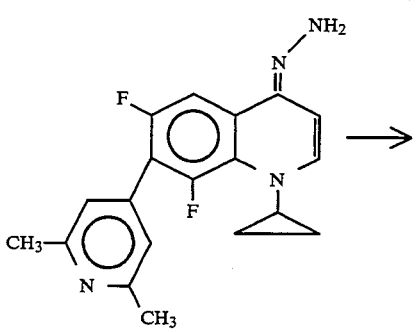

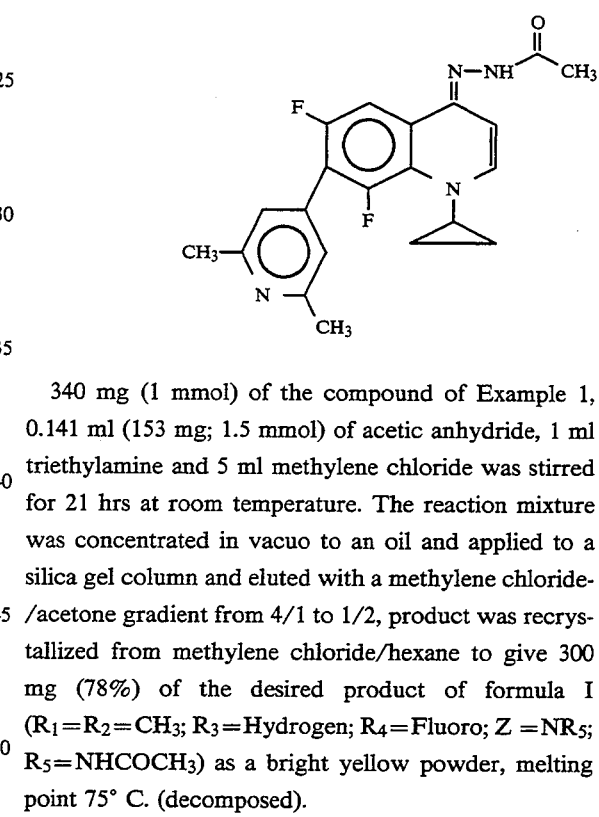

340 mg (1 mmol) of the compound of Example 1, 0.141 ml (153 mg; 1.5 mmol) of acetic anhydride, 1 ml triethylamine and 5 ml methylene chloride was stirred for 21 hrs at room temperature. The reaction mixture was concentrated in vacuo to an oil and applied to a silica gel column and eluted with a methylene chloride/acetone gradient from 4/1 to 1/2, product was recrystallized from methylene chloride/hexane to give 300 mg (78%) of the desired product of formula I ($R_1=R_2=CH_3$; $R_3=$Hydrogen; $R_4=$Fluoro; $Z=NR_5$; $R_5=NHCOCH_3$) as a bright yellow powder, melting point 75° C. (decomposed).

EXAMPLE 6

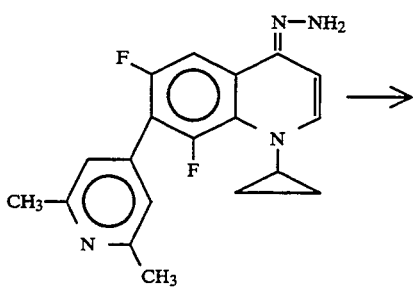

-continued

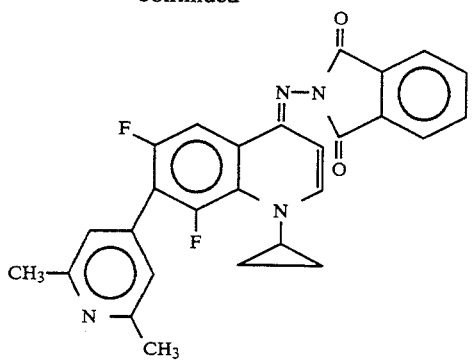

340 mg (1 mmol) of the compound of Example 1 and 148 mg (1 mmol) phthalic anhydride were taken up in 10 ml THF and stirred at room temperature for 15 hrs. 3 g SiO$_2$ was added to the reaction mixture and the mixture was heated to 80° C. for 20 hrs. The solvent was then stripped off and the residue taken up in methylene chloride and applied to a silica gel column. The column was washed with 10/1 methylene chloride/acetone and then eluted with 6/1 methylene chloride/acetone to give a yellow solid after solvent removal. This solid was recrystallized from methylene chloride/hexane to give 258 mg (71%) of a bright yellow powder, melting point 244°-246° C. (formula I: $R_1=R_2=CH_3$; $R_3=$Hydrogen; $R_4=$Fluoro; $Z=NR_5$; $R_5=$phthalimide)

EXAMPLE 7

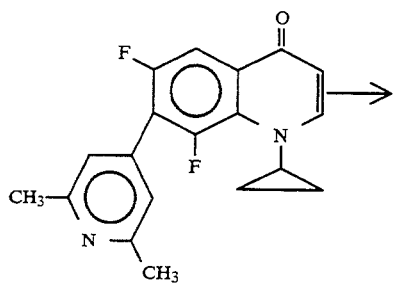

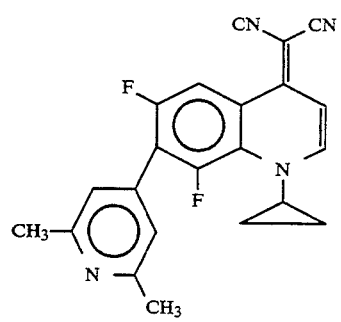

196 mg (0.6 mmol) of Intermediate A' (formula A; $R_1=R_2=CH_3$; $R_3=$Hydrogen; $R_4=$Fluoro), 396 mg (6 mmol) of malonitrile and 3 ml acetic anhydride were heated at 110° C. for 2 hrs. Excess reagents were stripped off and the residue was partitioned between chloroform and aqueous NaOH. The aqueous layer was extracted twice with chloroform and organic fractions were pooled, dried, concentrated and then crystallized from methylene chloride and ethyl/acetate. The filtrate (from crystal collection) was applied to a silica gel column and eluted as an orange band with ethyl acetate. Crystals and eluted product were recrystallized from ethyl acetate/methylene chloride to give 187 mg (83%) of a yellow solid of formula I ($R_1=R_2=CH_3$; $R_3=$Hydrogen; $R_4=$Fluoro; $Z=CR_6R_7$; $R_6=R_7=CN$), melting point 263°-264° C.

EXAMPLE 8

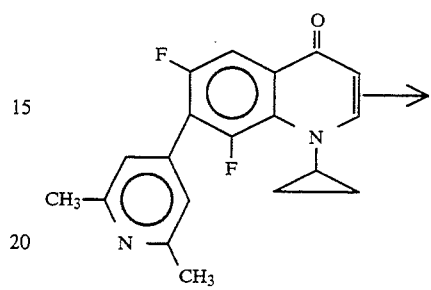

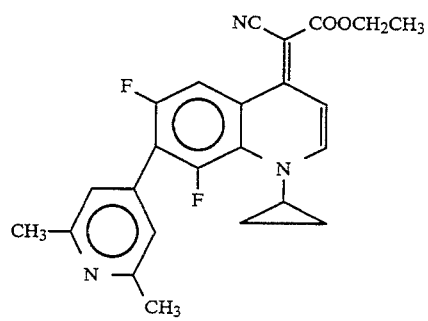

a) 326 mg of Intermediate A' (formula A; $R_1=R_2=CH_3$; $R_3=$Hydrogen; $R_4=$Fluoro), 1.0 ml NCCH$_2$COOEt and 4 ml acetic anhydride was heated to 130° C. for 9 hrs, cooled and concentrated in vacuo. The residue was applied to silica gel and eluted with 1/1 ethyl acetate/toluene. The appropriate fractions were crystallized from methylene chloride/ethyl acetate, giving 370 mg (79%) of a yellow solid of formula I, ($R_1=R_2=CH_3$; $R_3=$Hydrogen; $R_4=$Fluoro; $Z=CR_6R_7$ $R_6=$CN; $R_7=$CO$_2$CH$_2$CH$_3$), melting point 235°-238° C.

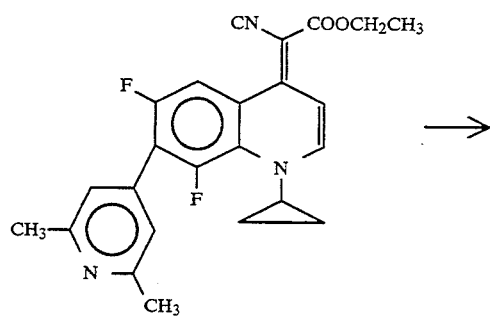

-continued $R_5NH_2$ (method B), or by the reaction of Intermediate A with an isocyanate $R_5NCO$ (method C). Abbreviations appearing in the table are defined as follows: tBuOMe; t-butyl methyl ether; ETOH; ethanol.

Preparation of example compounds of Formula I

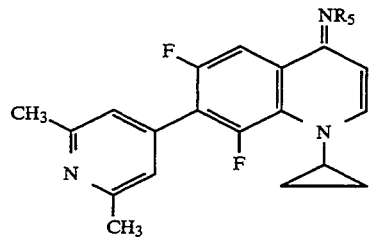

| Example # | $R_5$ | Method | Yield (%) | Recrystallizing Solvent | m.p. |
|---|---|---|---|---|---|
| 9 | $NHCH_3$ | A | 73 | $CH_2Cl_2$/Hexane | 171–174 |
| 10 | OH | B | 40 | EtOH/Hexane | 240(decom) |
| 11 | $N(CH_3)_2$ | B | 72 | $CH_2Cl_2$/Acetone | 173–175 |
| 12 | $c\text{-}C_3H_5$ | B | 50 | $CH_2Cl_2$/Hexane | 230(decom) |
| 13 | $NHCONH_2$ | B | 70 | $CH_2Cl_2$/Hexane | 190–192 |
| 14 | NH-9-acridinyl | B | 62 | $CH_2Cl_2$/Hexane | 275(decom) |
| 15 | $NH(CH_2)_2OH$ | B | 35 | $CH_2Cl_2$/Hexane | 154(decom) |
| 16 | NH-3-quinolinyl | B | 42 | ETOH/Hexane | 234–236 |
| 17 | $OCH_3$ | B | 63 | ETOH | 197–199 |
| 18 | S-4-Cl—Ph | B | 54 | $CH_2Cl_2$/Hexane | 222–224 |
| 19 | S-2-pyridinyl | B | 19 | $CH_2Cl_2$/Hexane | 234–236 |
| 20 | $(CH_2)_2N(CH_3)_2$ | B | 50 | $CH_2Cl_2$/Hexane | 155(decom) |
| 21 | $(CH_2)_3N(CH_3)_2$ | B | 60 | EtOAc/Hexane | 72–74 |
| 22 | Ph | C | 45 | t-BuOMe | 171–174 |
| 23 | 2-pyridinyl | B | 62 | $CH_2Cl_2$/Hexane | 189–190 |
| 24 | 2-OH—Ph | B | 86 | $CH_2Cl_2$/Hexane | 151–155 |
| 25 | 4-$NH_2$—Ph | B | 75 | $H_2O$ | 106–110 |

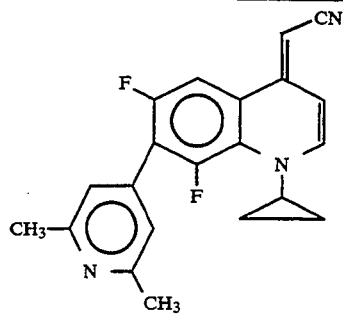

b) 214 mg of the compound of Example 8a, 3 ml 5% KOH and 7 ml dioxane were heated to 105° C. for 1½ hrs. The solvent was stripped off and the residue was partitioned between ethyl acetate/ether and water. The water phase was extracted thrice with ethyl acetate, acidified with acetic acid and extracted 5 times with ethyl acetate, then neutralized with sodium bicarbonate and extracted thrice more with ethyl acetate. All organic phases were combined, dried and concentrated in vacuo. The residue was chromatographed on silica using 70% ethyl acetate/hexane and recrystallized from ether/ethyl acetate yielding 155 mg (87%) of the desired product of formula I ($R_1=R_2=CH_3$; $R_3$=Hydrogen; $R_4$=Fluoro; $Z=CR_6R_7$ $R_6$=CN; $R_7$=H) as a yellow solid, melting point 163.5°–164.5° C.

EXAMPLES 9–25

The following compounds of formula I wherein Z is $NR_5$ were prepared by the reaction of Intermediate B' (formula B: $R_1=R_2=CH_3$; $R_3$=Hydrogen; $R_4$=Fluoro) and hydrazine $R_8R_9NNH_2$ (method A) or by the reaction of Intermediate C' (formula C: $R_1=R_2=CH_3$; $R_3$=Hydrogen; $R_4$=Fluoro; $R'=CH_3$; $X^-=I^-$) with either hydrazine $R_8R_9NNH_2$ or amine It is contemplated that compounds of formula I wherein Z is $CR_6R_7$ can be prepared by the methods of Examples 7 and 8 by reacting Intermediate A any of the following well known compounds.

| Reagent | $R_6$ | $R_7$ |
|---|---|---|
| $O_2NCH_2NO_2$ | $NO_2$ | $NO_2$ |
| $CH_3COCH_2NO_2$ | $NO_2$ | $CH_3CO$ |
| $C_6H_5CH_2NO_2$ | $NO_2$ | $C_6H_5$ |
| $CH_3CH_2NO_2$ | $NO_2$ | $CH_3$ |
| $CH_3COCH_2COCH_3$ | $CH_3CO$ | $CH_3CO$ |
| $C_6H_5COCH_2COCH_3$ | $CH_3CO$ | $C_6H_5$ |
| $CH_3NO_2$ | $NO_2$ | H |
| $CH_3COCH_2CO_2CH_2CH_3$ | $CO_2CH_2CH_3$ | $CH_3CO$ |
| $CH_2(SO_2CH_2CH_3)_2$ | $SO_2CH_2CH_3$ | $SO_2CH_2CH_3$ |

Biological Properties

Topoisomerase II has been identified as the cellular target for a number of therapeutically important antineoplastic classes of drugs (Glisson and Ross, Pharmacol. Ther. 32, 89–106, 1987; Liu, Ann. Rev. Biochem. 58, 351–375, 1989). These chemically distinct agents include intercalating anthracyclines, aminoacridines, and ellipticines as well as the non-DNA intercalating epipodophyllotoxins. The intracellular effects of these agents (Zwelling et al., Biochem. 29, 6553–6563, 1981; Long et al., Biochem 23, 1183–1188, 1984; Rowe et al. Biochem. Pharmacol. 34, 2483–2487, 1985; Rowe et al., Cancer Res. 46, 2021–2026, 1986; Kerrigan et al., NCI Monographs 4:117–121, 1987; Covey et al., Cancer Res. 48, 860–865, 1988), in addition to their topoisomerase II reactivity in vitro (Nelson et al., Proc. Natl. Acad. Sci.

81, 1361–1365, 1984; Tewey et al., J. Biol. Chem. 259, 9182–9187, 1984a; Tewey et al., Science 266, 466–468, 1984b; Ross et al., Cancer Res. 44, 5857–5860, 1984; Chen et al., J. Biol. Chem. 259, 13560–13566, 1984; Rowe et al., Cancer Res. 46, 2021–2026, 1986), implicate topoisomerase II inhibition as central to the cytotoxicity and antitumor activity of these antineoplastic agents. Additionally the mechanisms of resistance observed in several antineoplastic agent resistant cell lines appears to be a consequence of either an alteration in the topoisomerase enzyme molecule (Pommier et al., Cancer Res. 46, 3075–3081, 1986; Glisson et al., Cancer Res. 46, 1934–1938, 1986; Esty et al., Biochem. Biophys. Res. Commun. 144, 787–793, 1987; Danks et Biochem. 27, 8861–8869, 1988; Sinha et al., Cancer Res. 48, 5096–5100, 1988) or its level (Per et al., Mol. Pharmacol. 32, 17–25, 1987). This evidence has clearly established topoisomerase II inhibition as a means of deriving an antitumor effect.

The compounds of the invention are inhibitors of mammalian topoisomerase II thus indicating their use as cytotoxic and antineoplastic agents in the chemotherapy of cancer in mammals.

Mammalian Topoisomerase II Inhibition Assay Procedure

The inhibition of human topoisomerase II (hereafter topo II) was quantitated by a procedure adapted from that described by Trask et al., EMBO J., 3, 671–676 (1984). The assay quantitates the amount of topo II covalently complexed by DNA at equilibrium during a topo II reaction. This assay determines the potential of a compound to stabilize this complex, which potential is closely related to the cytotoxicity of several clinically useful antineoplastic agents.

Topo II was purified from late log phase suspension cultures of HeLa WIS by an adaptation of the method described by Per et al., Mol. Pharmacol., 32, 17–25 (1987).

Assays (in duplicate) were assembled at 4° C. Assay mix (25 μl) was distributed in Beckman (No. 265270) 1.5 mL microtitre tubes followed by the addition of 5 μl test to yield the final concentrations of assay components:

50 mM Tris-Cl pH 7.9
44 mM NaCl
10 mM MgCl
0.6 mM DTT
0.5 mM EDTA
30 μg/ml BSA
0.5 mM ATP
5.5 % (w/v) glycerol
4 ng 3' end labeled ($^{32}$p) pBR$_{322}$ DNA ($10^7$ DPM/μg)
10 units Topo II The assay mix including the test compound was incubated for 20 minutes at 37° C. The reaction was terminated at 37° C. by the addition of 3 μl 10% SDS followed by the addition of 266 μl 10 mM Tris-Cl pH 7.5, 20 μg/ml calf thymus DNA, 1% SDS.

A SDS/protein precipitate was formed by the addition of 28 μl 2.5M KCl followed by chilling on ice for a minimum of 10 minutes. The precipitate was collected and washed with a Brandell cell harvester on a GFB glass fiber filter membrane as follows. The contents of the assay tube were drawn up into the harvester. The tube was then rinsed 7× with 10 mM Tris-Cl pH 7.5, 1 mM EDTA and 100 mM KCl. The precipitate was washed with 1 L of a solution of 10 mM Tris-Cl pH 7.5, 1 mMEDTA, 100 mM KCl followed by 1 L of 95% ethyl alcohol and finally 0.5 L 70% of ethyl alcohol (per 48 samples in each case). After drying, CPM was determined by liquid scintillation counting with 5 ml Biofluor (NEN Research Products) or Readisafe (Beckman Instruments Inc.) cocktail.

Preparation of test compound—A stock solution (6 mg/ml) of test compound was prepared either in 0.1N sodium hydroxide or 0.2N hydrogen chloride. This solution then was diluted 1/5 into water and serially thereafter in either 0.02N sodium hydroxide or 0.04N hydrogen chloride, respectively. The stock solution and serial dilution of the test compound was stored at −20° C. prior to testing.

Screening of test compound—As an initial screen, the test compound was tested at a final concentration of 2, 20 and 200 μg/ml. The compound was then retested at a range of concentrations (usually 2–3× steps) bridging their approximate EC$_{50}$'s, as estimated by the prescreen.

Controls—A solvent control which indicates the base level of topo II-DNA complexes formed in the absence of the test compound was included in each test. A control, in which topo II was omitted, was included for each test compound at the highest drug concentration tested.

Reference Agent—A dose response curve with mAMSA at 0.01, 0.08, 0.16, 0.32, 1.0 and 10 μg/ml was included in each test.

Data reduction—The EC$_{50}$ (effective concentration at which 50% of the maximal DNA-topo II complex is formed) of a test compound is defined to be the concentration with activity equal to the EC$_{50}$ of the reference agent, mAMSA. The maximal DNA-topo II complex formed is taken as that equal to that formed at the nearly saturating dose of mAMSA (10 μg/ml).

The results obtained for representative compounds of the invention in the human topoisomerase II assay procedure expressed as EC$_{50}$s (μM) are presented in Table 3.

Representative examples of the compounds of formula I were also tested for antitumor activity in mice against several tumor systems, as described more fully below, and were found to be inactive.

In vivo Antitumor Assay Procedure

Mice: Inbred: C3H/He and NCR-nu; and Hybrids: B6D2F1 (C57BL/6 females×DBA/2 males, CD2F1 (Balb/c females×DBS/2 males) and B6C3fl (C57BL/6×C3H) were bred at Wayne State University from strains obtained from the Frederick Cancer Research Facility, Frederick, Md. or purchased from commercial suppliers.

Tumors: Murine Tumor: P388 leukemia and pancreatic ductal adenocarcinoma No. 03 (Panc 03) were used for in vivo testing. Human tumor: A single human tumor, mammary carcinoma MX-1 (MX1) was used for in vivo testing. All tumors are in the Developmental Therapeutics Program frozen tumor respository, maintained by the Biological Testing Branch, Frederick, Md. Each has a detailed description, code identification number, and list of references at the National Tumor Repository. Murine tumors were maintained in the mouse strain of origin and were transplanted in the appropriate F1 hydrid (or the strain of orgin) for therapy trials. Human mammary carcinoma MX-1 (MX1) was maintained as a subcutaneous implant in either athymic Swiss (Cr: NIH (S) - nu) or athymic random bred (NCR-nu) mice and transplanted in NCR-nu for therapy trials.

Chemotherapy: For pancreatic ductal adenocarcinoma No. 3, bilateral tumor implants were used to help ensure a more uniform tumor burden per mouse. The animals necessary to begin an experiment were pooled, implanted bilaterally s.c. on day zero with 30–60-mg tumor fragments using a 12-gauge trocar, and again pooled before randomization to the various treatment and control groups. Chemotherapy was started within three days after tumor implantation while the number of cells per mouse was relatively small ($1 \times 10^7 - 1 \times 10^8$ cells).

For P388 leukemia studies the tumor cells were implanted intraperitoneally on day zero and treatment was started on day one. Titered controls were also included to facilitate the calculation of tumor cell kill. For mammary carcinoma MX-1 studies, tumors were implanted subcutaneously (sc) (14-mg fragment of s.c. donor tumor) in the axillary region. Treatment started on the day when the subcutaneous tumor implant had reached 100-700 mg.

End Points for Assessing Antitumor Activity

Quantitative end points used to assess antitumor activity were percent Increased Life Span (% ILS), and Tumor Growth Inhibition (T/C).
Endpoints were calculated as follows:
% ILS $$\% \, ILS + \frac{D_t - D_c}{D_c} (100)$$

where Dt is the median day of death for treated and Dc is the median day of death for control groups. A % ILS $\geq 20$ for the P388 intraperitoneal model is indicative of a significant degree of antitumor activity. A % ILS $\geq 75$ for the P388 intraperitoneal model, is indicative of a high degree of antitumor activity and is the level used by National Cancer Institute to justify further development if other requirements are met (termed DN-2 level activity).

T/C Value

Tumors were measured with a caliper once or twice weekly (as needed) until either tumors exceeded 1600 mg or cure was assured. Tumor weights were estimated from two dimensional measurements: Tumor Weight (mg)+(a×b²)/2, where a and b are the tumor length and width (mm) respectively. Measurements were carried out simultaneously in both treatment and control groups. When the control group tumors reached approximately 750–1500 mg in size (median of group), the median tumor weight of each group was determined (including zeros). The T/C value in percent is an indication of antitumor effectiveness. The % T/C was calculated from the following formula for solid murine tumor models:

$$\% \, T/C = \frac{T}{C} \times 100$$

where T and C are median tumor weights of the treatment and control groups, respectively. A T/C equal to or less than 42% is considered significant antitumor activity. A T/C value < 10% is indicative of a high degree of antitumor activity and is the level used by National Cancer Institute to justify further development if other requirements are met (termed DN-2 level activity). By convention the T/C value for the mammary carcinoma MX-1 model is calculated by the parameter of change in tumor weight. The % T/C was calculated from the following formula for the MX-1 model;

$$\% \, T/C = \frac{\Delta T}{\Delta C} \times 100 \text{ (if } \Delta T \text{ is positive)}$$

$$\% \, T/C = \frac{\Delta T}{T \text{ (initial)}} \times 100 \text{ (if } \Delta T \text{ is negative)}$$

where $\Delta T$ and $\Delta C$ are the change in mean tumor weight of the test and control groups, respectively, and T (initial) is the initial mean tumor weight of the test group. Art initial % T/C $\leq 20$ is considered to demonstrate moderate activity. A % T/C $\leq 10$ is considered significant activity.

All in vivo trials are summarized in Table 3 below.

TABLE 3

| Example | Topo II EC$_{50}$ ($\mu$M) | In vivo antitumor activity |
|---|---|---|
| Int A | 17 | Inactive Panc03 |
| Int B | 76$^E$ | Not tested |
| Int C | 24 | Not tested |
| 1 | 1.7 | Inactive Panc03 sc tumor/iv drug |
| 2 | 0.98 | 37% T/C Panc03 sc tumor/iv drug Inactive P388 ip tumor/ip drug Inactive P388 ip tumor/iv drug Inactive MX-1 sc tumor/ip drug |
| 3 | 45* | Not tested |
| 4 | 12 | Not tested |
| 5 | 20 | Not tested |
| 6 | 16 | Not tested |
| 7 | 6.3* | Not tested |
| 8a | 4.8* | Not tested |
| 8b | 4.0 | Not tested |
| 9 | 1.9 | Not tested |
| 10 | 1.4 | Inactive Panc03 sc tumor/iv drug |
| 11 | 2.3 | Not tested |
| 12 | 2.4 | Inactive Panc03 sc tumor/iv drug |
| 13 | 3.1 | Inactive Panc03 sc tumor/iv drug |
| 14 | 28 | Not tested |
| 15 | 3.2 | Not tested |
| 16 | 92 | Not tested |
| 17 | 2.6* | Not tested |
| 18 | 9.4 | Not tested |
| 19 | 3.8 | Not tested |
| 20 | 14 | Not tested |
| 21 | 5.5 | Not tested |
| 22 | 1.9 | Not tested |
| 23 | 3.6 | Not tested |
| 24 | 1.6 | Not tested |
| 25 | 7.6 | Not tested |

$^E$endpoint of assay extrapolated.
*bell shaped dose response.

In practicing the method of the invention, the therapeutic dose of the compound of formula I to be administered to the mammal afflicted with malignant cells is that amount which is effective to inhibit mammalian topoisomerase II and thereby to inhibit the growth of, kill or induce the regression of the malignant cells, or to prolong the life of the mammal.

The specific amount of formula I constituting a therapeutically effective dose and the length of treatment required will vary since it is dependent on a number of factors such as, for example, the size, age, condition and species of the mammal to be treated, the degree of involvement of the malignancy, the specific compound to be administered and its bioavailability, the dose regimen and the mode of administration. The specific amount to be employed for a particular afflicted mammal is readily determinable by the skilled artisan using conventional techniques.

In practicing the invention, the compounds can be administered to the mammal orally or parenterally.

The pharmaceutical compositions are formulated for use by preparing a dilute solution or suspension in a pharmaceutically acceptable aqueous, organic or aqueous organic medium for topical or parenteral administration by intravenous or intramuscular injection, or for intranasal or ophthalmic application; or are prepared in tablet, capsule, or aqueous suspension form with conventional excipients for oral administration.

The compounds can be prepared for use by incorporating them in conventional, pharmaceutically acceptable diluents, carriers or excipients. For parenteral administration (intravenous, intraperitoneal, subcutaneous or intramuscular), the compounds are dissolved or suspended in an aqueous or nonaqueous vehicle. For oral administration, the compounds are formulated in dosage unit form as tablets or capsules. Exemplary diluents, carriers or excipients include lactose, dextrose, sucrose, sorbitol, mannitol, starches, gum acacia, calcium phosphate, mineral oil, cocoa butter, alginates, tragacanth, gelatin, methyl cellulose, methyl- and propyl hydroxybenzoates, talc, magnesium stearate and the like.

We claim:

1. A compound of formula;

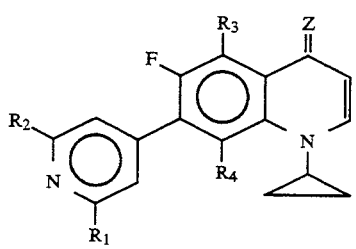

wherein;

$R_1$ is hydrogen, lower-alkyl, or trifluoromethyl;

$R_2$ is lower-alkyl, trifluoromethyl or $CH_2X$ where X is hydroxy, chloro, lower-alkylamino or dilower-alkyl-amino;

$R_3$ and $R_4$ are each individually hydrogen or fluoro;

Z is $NR_5$ or $CR_6R_7$;

$R_5$ is hydrogen, aryl, arylthio, arylsulfonyl, lower-alkyl, cycloalkyl, heterocycloalkyl, amino-lower-alkyl, lower-alkylamino-lower-alkyl, dilower-alkylamino-lower-alkyl, lower-alkoxy, hydroxy or $NR_8R_9$;

$R_6$ is hydrogen, cyano, lower-alkoxycarbonyl, lower-alkanoyl, nitro or lower-alkylsulfonyl;

$R_7$ is hydrogen, cyano, lower-alkoxycarbonyl, lower-alkanoyl, nitro, aryl, or lower-alkylsulfonyl;

$R_8$ is hydrogen, lower-alkyl, aryl, heterocycloalkyl, carbamyl, alkanoyl, aroyl, hydroxy-lower-alkyl; and $R_9$ is hydrogen, lower-alkyl or lower-alkanoyl or a pharmaceutically acceptable acid addition salt thereof.

2. A compound according to claim 1 wherein $R_1$ and $R_2$ are methyl, $R_3$ is hydrogen, and $R_4$ is fluoro.

3. A compound according to claim 2 wherein Z is $NR_5$.

4. A compound according to claim 3 wherein $R_5$ is hydrogen, aryl, arylthio, arylsulfonyl, lower-alkyl, cycloalkyl, amino-lower-alkyl, lower-alkylamino-lower-alkyl, dilower-alkylamino-lower-alkyl or lower-alkyloxy.

5. A compound according to claim 4 wherein $R_5$ is arylthio, arylsulfonyl, hydroxy or $NR_8R_9$.

6. A pharmaceutical composition comprising a pharmaceutical carrier and an effective amount of a compound according to claim 1.

7. A pharmaceutical composition comprising a pharmaceutical carrier and an effective amount of a compound according to claim 2.

8. A pharmaceutical composition comprising a pharmaceutical carrier and an effective amount of a compound according to claim 3.

9. A pharmaceutical composition comprising a pharmaceutical carrier and an effective amount of a compound according to claim 4.

10. A pharmaceutical composition comprising a pharmaceutical carrier and an effective amount of a compound according to claim 5.

* * * * *